US008247217B2

(12) United States Patent
Ceremony et al.

(10) Patent No.: US 8,247,217 B2
(45) Date of Patent: Aug. 21, 2012

(54) THERMAL CYCLER WITH SELF-ADJUSTING LID

(75) Inventors: Jeffry M. Ceremony, Fairfield, CA (US); Daniel Y. Chu, Hercules, CA (US); Deepak K. Doshi, Hercules, CA (US); Rhoel Rumbaoa, Fairfield, CA (US); Dennis W. Loring, Martinez, CA (US); Paul J. Patt, Blackhawk, CA (US); Cliff Baldwin, Oakpoint, TX (US)

(73) Assignee: Bio-Rad Laboratories, Inc., Hercules, CA (US)

(*) Notice: Subject to any disclaimer, the term of this patent is extended or adjusted under 35 U.S.C. 154(b) by 519 days.

(21) Appl. No.: 12/370,790

(22) Filed: Feb. 13, 2009

(65) Prior Publication Data

US 2009/0269835 A1 Oct. 29, 2009

Related U.S. Application Data

(60) Provisional application No. 61/029,128, filed on Feb. 15, 2008.

(51) Int. Cl.

| | |
|---|---|
| ***C12M 1/36*** | (2006.01) |
| ***C12M 1/02*** | (2006.01) |
| ***C12M 1/00*** | (2006.01) |
| ***C12M 3/00*** | (2006.01) |
| ***F27D 11/00*** | (2006.01) |

(52) U.S. Cl. ............... 435/286.2; 435/286.1; 435/287.2; 435/288.3; 435/288.4; 435/303.1; 219/428

(58) Field of Classification Search ............... 435/286.1, 435/286.2, 303.1, 287.2, 288.2, 288.3, 288.4; 219/428

See application file for complete search history.

(56) References Cited

U.S. PATENT DOCUMENTS

| | | | |
|---|---|---|---|
| 6,197,572 | B1 | 3/2001 | Schneebeli |
| 6,423,536 | B1 | 7/2002 | Jovanovich et al. |
| 7,081,600 | B2 | 7/2006 | Brown et al. |
| 2004/0112969 | A1 | 6/2004 | Saga et al. |
| 2008/0003649 | A1 | 1/2008 | Maltezos |

*Primary Examiner* — Michael Marcheschi
*Assistant Examiner* — Gautam Prakash
(74) *Attorney, Agent, or Firm* — Kilpatrick Townsend & Stockton LLP.; M. Henry Heines

(57) ABSTRACT

A thermal cycling instrument for PCR and other reactions performed on multiple samples with temperature changes between sequential stages in the reaction procedure is supplied with a thermal block to provide rapid changes and close control over the temperature in each sample vessel and a pressure plate incorporated into a motorized lid that detects anomalies in the reaction vessels or in their positioning over the thermal block, and automatically adjusts the plate position to achieve an even force distribution over the sample vessels.

15 Claims, 13 Drawing Sheets

THERMAL CYCLER WITH SELF-ADJUSTING LID

CROSS-REFERENCE TO RELATED APPLICATION

This application claims the benefit of U.S. Provisional Patent Application No. 61/029,128, filed Feb. 15, 2008, the contents of which are incorporated herein by reference.

BACKGROUND OF THE INVENTION

1. Field of the Invention

This invention relates to laboratory equipment used for performing sequential chemical reactions of which the polymerase chain reaction (PCR) is an example. In particular, this invention relates to thermal cyclers for such reactions, and to methods and apparatus for controlling the temperature in each of a multitude of reaction vessels in which rapid and accurate temperature changes are needed.

2. Description of the Prior Art

PCR is one of many examples of chemical processes that require precise temperature control of reaction mixtures with rapid and precise temperature changes between different stages of the process. PCR itself is a process for amplifying DNA, i.e., producing multiple copies of a DNA sequence from a single strand bearing the sequence. PCR is typically performed in instruments that provide reagent transfer, temperature control, and optical detection in a multitude of reaction vessels such as wells, tubes, or capillaries. The process includes a sequence of steps that are temperature-sensitive, different steps being performed at different temperatures and the sequence being repeated a multitude of times to obtain a quantity large enough for analysis and study from an extremely small starting quantity.

While PCR can be performed in any reaction vessel, multi-well reaction plates are the reaction vessels of choice. In many applications, PCR is performed in "real-time" and the reaction mixtures are repeatedly analyzed throughout the process, using the detection of light from fluorescently-tagged species in the reaction medium as a means of analysis. In other applications, DNA is withdrawn from the medium for separate amplification and analysis. Multiple-sample PCR processes in which the process is performed concurrently in a number of samples can be performed by placing each sample in one well of a multi-well plate or plate-like structure and simultaneously equilibrating all samples to a common thermal environment in each step of the process. The samples can also be exposed to two thermal environments simultaneously to produce a temperature gradient across each sample. An alternative to multi-well sample plates are individual plastic tubes held together by a tube rack or support or simply individually placed in a common block of high thermal conductivity known as a "thermal block" (described below) that controls the temperature.

In the typical PCR instrument, either a multi-well plate (usually one with 96 wells in an 8×12 array, but often ones with larger or smaller numbers of wells) with a sample in each well or a series of individual plastic tubes is placed in contact with the thermal block. The thermal block is heated and cooled either by a Peltier heating/cooling apparatus, which may be a single Peltier module or an array of modules, or by a closed-loop liquid heating/cooling system that circulates a heat transfer fluid through channels machined into the block. In either case, the heating and cooling of the thermal block are typically under the control of a computer with input from the operator. The thermal block makes intimate contact with the plate wells or the tubes to achieve maximal heat transfer. The reaction vessels, whether they be a plate or individual tubes, are usually plastic which itself is not a medium of high thermal conductivity. The plastic itself, plus the interface between the plastic and the metallic thermal block, produces thermal resistance which must be reduced or at least controlled to achieve efficient heat transfer between the thermal block and the reaction media. Reduction and control of the thermal resistance can be achieved by applying force to the vessels to press the vessels against the corresponding depressions in the thermal block. The force must be applied evenly to achieve uniform temperature control and minimal thermal resistance. The same force also serves to help seal the vessels during the thermal cycling and to maintain the seal during the pressure changes that result from the heating and cooling stages of the thermal cycling. The force must be adequate to serve all of these purposes, and the thermal cycler, which term is commonly used to denote the instrument in which the entire PCR process is performed, must also be able to accommodate reaction tubes or plates of different heights, and also to allow the operator to select the magnitude of the force to be applied. The optimal thermal cyclers are those that are automatically operated with safeguards against user error.

SUMMARY OF THE INVENTION

The present invention resides in apparatus for performing temperature-controlled multi-vessel reactions, the apparatus including (a) a base designed to receive sample vessels in the form of a multi-well plate or individual sample tubes and that contains, or is configured to hold in a fixed position, a thermal block with associated temperature control, and (b) a lid that covers the base, the thermal block, and the sample vessels and incorporates a self-leveling pressure plate for the vessels that seals the tops of the vessels. The lid is motorized in certain embodiments of the invention. When individual tubes are used as the vessels, the tubes are capped, and the pressure plate presses on and thereby seals the caps. When the vessels are the wells of a multi-well plate, the wells are typically sealed with a sealing tape or with caps, and the pressure plate enforces the seal by pressing on the sealing tape. The pressure plate also presses the vessels into the indentations of the thermal block, and by virtue of the self-leveling feature, applies pressure to all of the vessels with a uniform force distribution to achieve optimal contact between each vessel and the thermal block. In preferred embodiments of the invention, the apparatus further contains a heating system for the pressure plate to prevent condensation of the vessel contents on the pressure plate due to the heating and cooling cycles that the apparatus performs during the reaction procedures. Still further embodiments include an optical scanning mechanism for optical monitoring of all of the vessels. Additional features that are present in preferred embodiments include a motorized latch to hold the lid in a closed position over the base, a motorized support connecting the pressure plate to the lid to adjust the height of the pressure plate in accordance with the height of the tubes or the plate, sensors for various functions, and a microprocessor to engage or disengage the various motors in response to signals received from the sensors. The invention also resides in pressure plates of specialized construction to maximize the transfer of heat toward the vessels and to assure that the force distribution is uniform along the length and width of the plate. These and other features are explained in more detail below.

DETAILED DESCRIPTION OF THE INVENTION AND PREFERRED EMBODIMENTS

Figure 1:
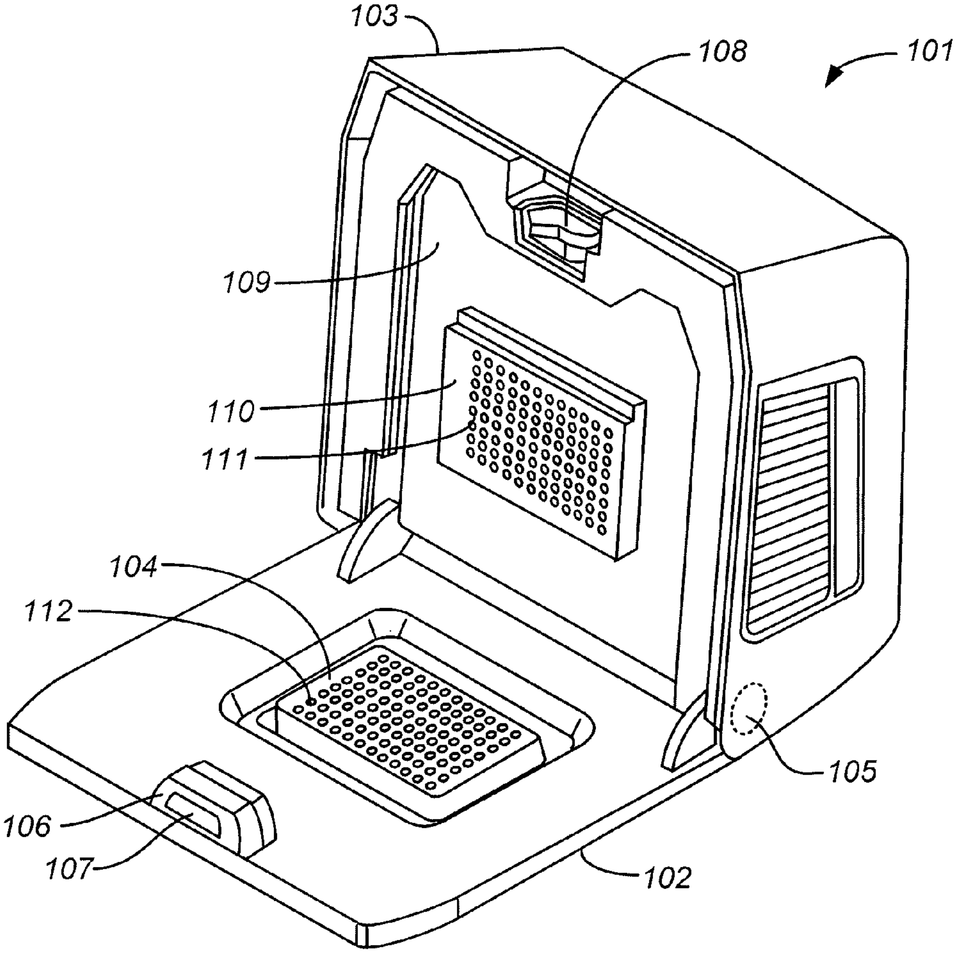
FIG. 1 is a perspective view of an instrument in accordance with the present invention with the lid raised. The remaining Figures show components of this instrument.

While the features defining this invention are capable of implementation in a variety of constructions, the invention as a whole will be best understood by a detailed examination of a specific embodiment. One such embodiment is shown in the drawings.

FIG. 1 depicts an instrument embodying the features of the invention, showing the enclosure or shell 101 which includes a base 102 and the aforementioned lid 103. Residing within the base 102 in a fixed position is a thermal block 104 that is heated and cooled from underneath by Peltier modules (not visible) that contact the base through a thermally conductive pad or grease to enhance the thermal conductivity, the Peltier modules themselves being in contact with cooling fins (also not visible) to dissipate waste heat expelled by the modules. Alternatives to Peltier modules are channels for a heat transfer fluid and a circulation system for circulating the fluid between the channels and an external heating or cooling element. The thermal block 104 contains an array of indentations that are complementary in contour to the outer surfaces of the sample vessels (not shown), whether they be a multi-well plate or individual tubes, that will be placed on the thermal block for temperature cycling and control. The complementary contours permit continuous contact to be made between the sample vessels and the thermal block. The lid 103 is joined to the base 102 by a torsion spring hinge assembly 105 which includes a bearing-supported hinge motor and integrated sensor flags in conjunction with optical sensors to detect when the lid is open and closed. Alternatives to the hinge assembly are any connectors that permit raising and lowering of the lid over the base. In the embodiment shown, the lid is counterbalanced with a torsion spring, and the hinge is operated by a DC motor with an encoder to provide position signals for the lid. At the front of the base 102 is an open/close switch pod 106 with a spring-mounted front button 107. Contained within the switch pod 106 (and thus not visible) are a tactile momentary switch or a capacitative optical switch, and a printed circuit board (PCB) for the switch. The switch pod button 107 can be configured to initiate the entire motor sequence, beginning with the hinge motor and proceeding to the other motors and sensors, as programmed by a microprocessor. The hinge, if in the open position, can also be operated manually, and the motor circuit can include an open-disconnect to minimize any braking force caused by the back EMF that might occur during manual operation. Minimizing the braking force will also minimize any interference that the back EMF would create with the manual operation and will eliminate potential damage to the motor. The microprocessor can also provide the capability of actuating the hinge motor, much like the drawer in a compact disc changer, to override the manual operation of the hinge, by monitoring the counts transmitted by an encoder on the hinge motor. When changes in the counts are detected to indicate movement of the hinge position in either direction, an algorithm in the microprocessor is actuated that begins with actuation of the hinge motor and proceeds with the functions that position the lid. A functional description of the algorithm is described below.

Directly opposing the switch pod 106 is a front clamp 108 in the lid to effect the final clamping of the lid 103 over the base 102 and thereby to apply the force that will seal the sample vessels closed and press the vessels against the thermal block 104. The front clamp 108, which is shown in a separate drawing and described in detail below, is a geared disk with a cam-shaped track that engages a pin on the switch pod 106. The disk is driven by a DC motor with an encoder and contains two optical limit switches.

The pressure plate 109 which presses the reaction vessels against the thermal block and heats the tops of the vessels is supported by the lid 103 and has a downwardly facing central platform 110 that directly contacts the sample vessels. The central platform 110 has an array of holes 111 that are aligned with the indentations 112 in the thermal block and hence with the locations of the sample vessels. The holes 111 allow light to pass in both directions. Excitation light can thus be transmitted from a scanner to the samples in the sample vessels and emissions from the samples can be transmitted back to the scanner, which is also shown in a separate figure and described below. As an optional feature, the central platform 110 can be bordered by a skirt (not shown in the Figures) with a rubber baffle on the bottom of the skirt to serve as a supplementary lateral seal around the reaction vessels. This prevents heat flow across the edges of the plate due to conduction, convection, and air drafts. A further optional feature for use when the sample vessels are the wells of a multi-well plate is a gasket of rubber or foam adhering to the lower face of the pressure plate to contact the multi-well plate adjacent to its edge. The gasket will provide a sealing function and, with its resilient character, also add to the self-leveling character of the pressure plate.

Figure 2:
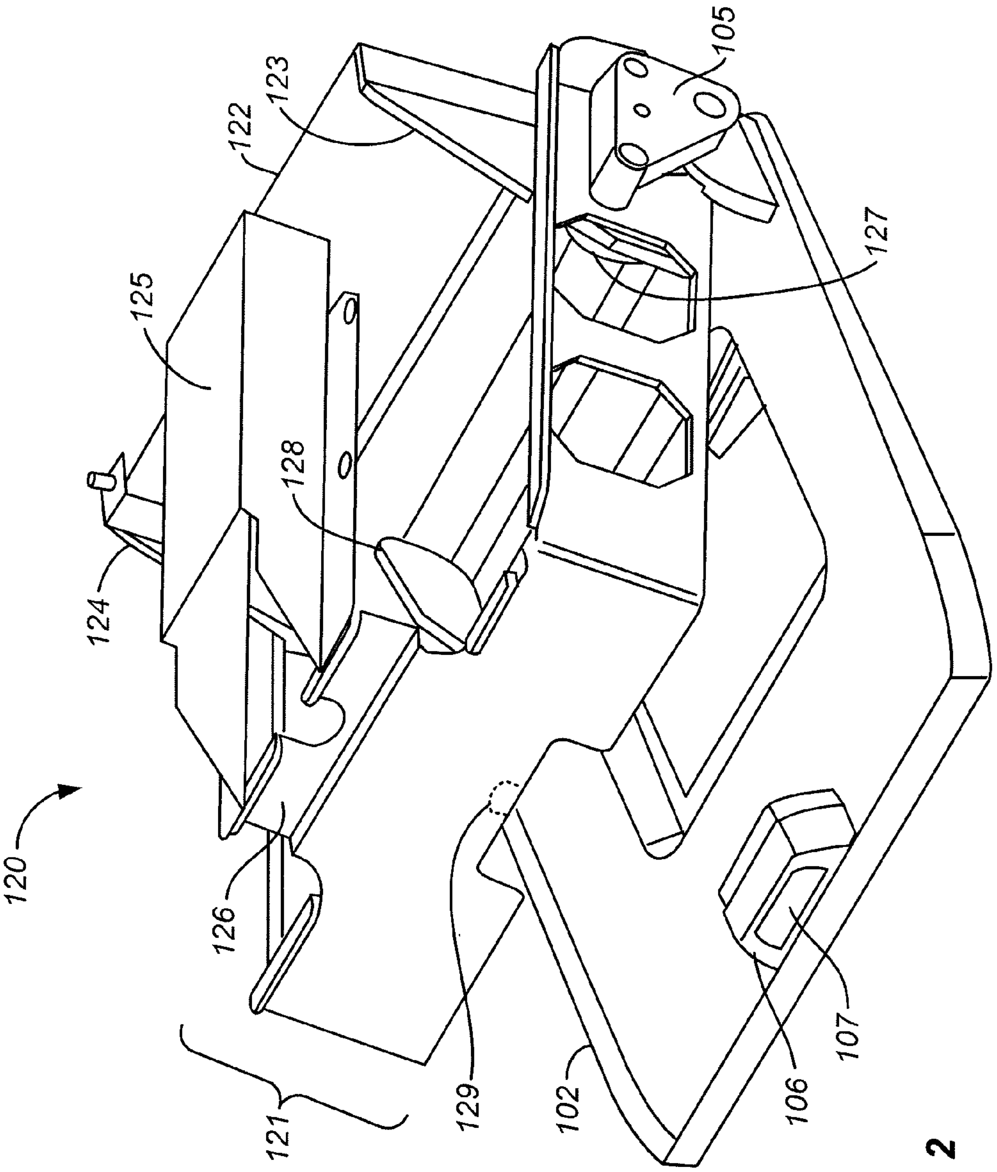
FIG. 2 is a perspective view of the main frame of the lid.

FIG. 2 depicts the main frame 120 of the instrument, with functional components removed to show the main structural frame 121 of the lid, the rear panel 122 of the lid, the hinges 123, 124 joining the lid to the base 102, and a support bracket 125 for internal components of the instrument. The support bracket 125 will be referred to herein as an "upper channel." The upper channel 125 is rigidly secured to the main structural frame 121 at the upper front end 126 of the frame and at the rear of the frame and serves as the mount for the positioning motor and self-leveling joint that control the position of the pressure plate. The pressure plate, positioning motor, and self-leveling joint are all shown in other figures and described below. An internal view of the hinge assembly 105 is also visible, together with the hinge motor 127 that drives the rotation of the hinge. The action of the hinge motor 127 is controlled in part by the sensors to detect the position of the lid. An open sensor 128 is affixed to the frame 121 inside a rear corner, and a closed sensor 129 is positioned on the front of the lid to be engaged upon contact with the switch pod 106. Both sensors are optical switches with associated flags of flexible material that causes the flags to bend upon contact and interrupt an optical beam. Other switches and flags known in the art are readily substituted.

Figure 3:
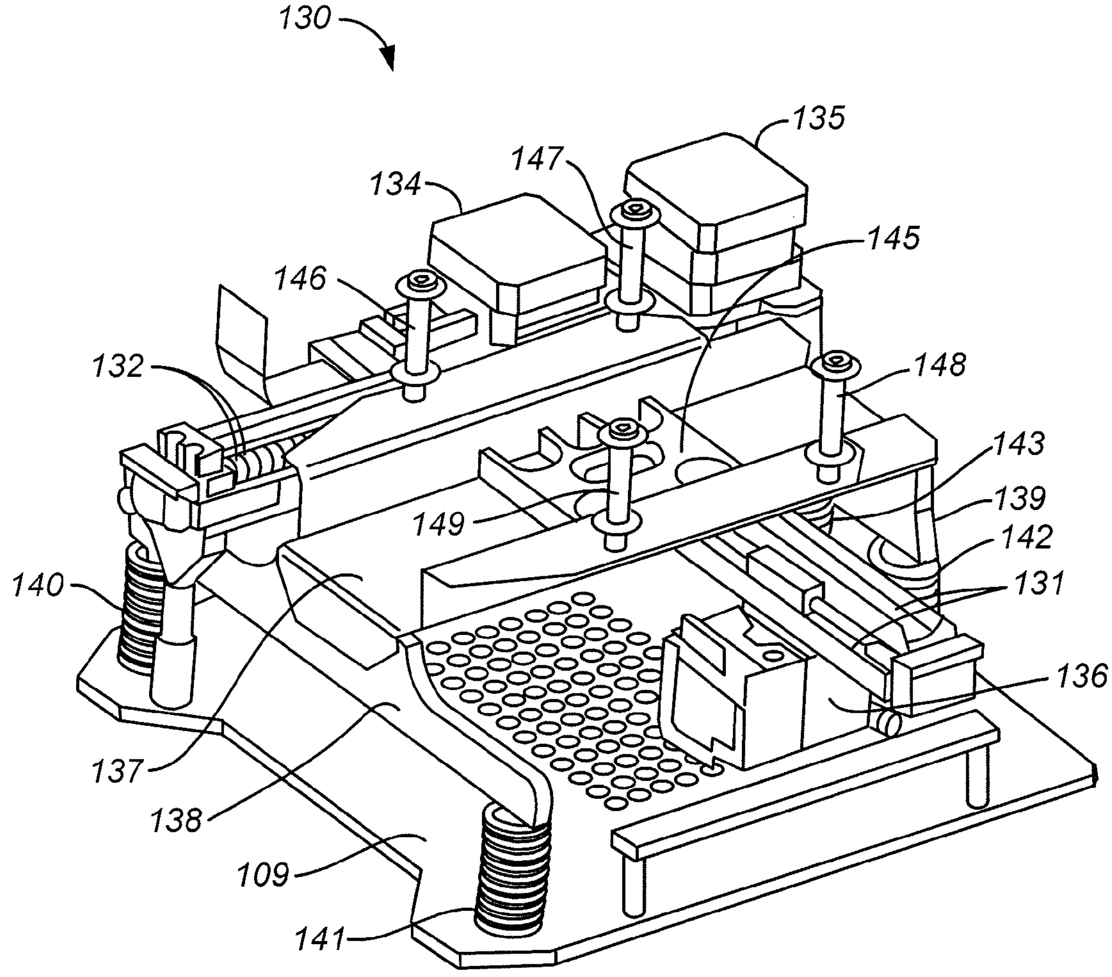
FIG. 3 is a perspective view of some of the lid components that are secured to or suspended by the main frame.

FIG. 3 depicts the lid heater carrier sub-assembly 130 which is supported by the main frame. This sub-assembly supports the heated pressure plate and the scanning mechanism. The scanning mechanism includes orthogonal rails 131, 132 that define the X and Y axes, respectively, of the scanning plane, plus two motor assemblies 134, 135, one for each of the scanning axes, and a shuttle 136 that contains the optical components and travels the rails. Connection of the sub-assembly to the main frame 120 of FIG. 2 is achieved through a bracket 137 referred to herein as a "lower channel" by virtue of its configuration and its position below the upper channel 125 of FIG. 2. The upper and lower channels are joined through a universal joint that functions as a self-leveling joint. The term "universal joint" is used herein to denote a join that can bend in any direction, i.e., one that bend and can also rotate a full 360°. This joint is shown in other Figures and is described below. The lower channel 137 is mounted to the pressure plate 109 through front and rear brackets 138, 139 and four coil springs 140, 141, 142, 143. The four coil springs transmit the force originating at the front clamp motor to the vessels. Secured to the floor of the lower channel 137 is a pivot block 145 which forms the lower portion of the self-leveling joint. The upper and lower channels 125, 137 are further joined by four guide posts 146, 147, 148, 149 in a non-rigid connection. The guide posts maintain the vertical alignment of the pressure plate 109 as the plate is leveled by the self-leveling joint. Each guide post is preferably surrounded by a coil spring (not shown) to help stabilize the upper and lower channels and to assist in distributing the force imposed by the pressure plate on the sample vessels and thermal block situated underneath.

Figure 4:
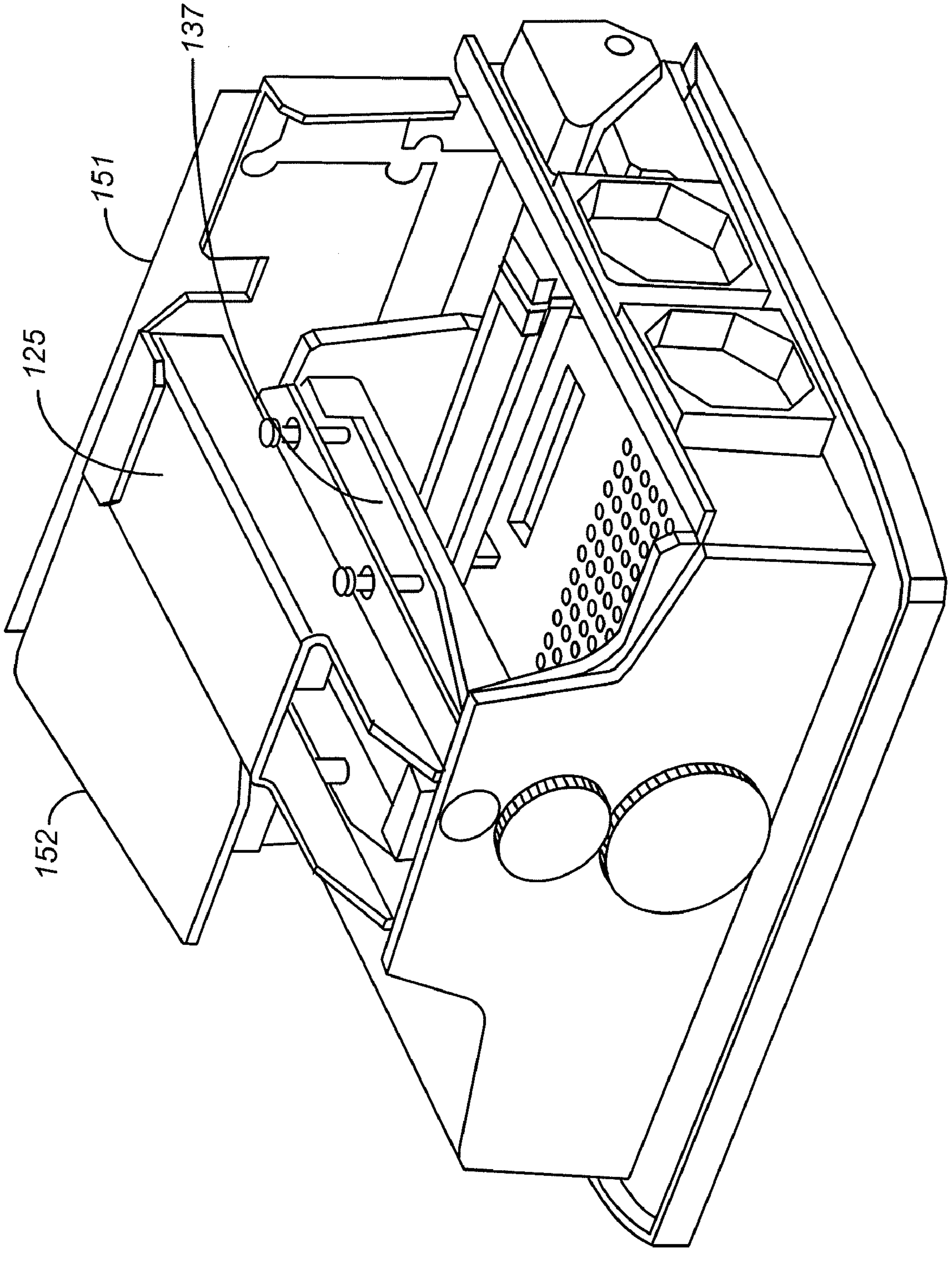
FIG. 4 is a perspective view of the frame assembly and lid components of FIG. 3 combined.

FIG. 4 depicts portions of the main frame 120 and the lid heater carrier sub-assembly 130 combined, as they would appear with the lid closed. Two printed circuit boards 151, 152, which together control the scanning and lid operations, are shown. The Figure also shows the relative positions of the upper channel 125 and the lower channel 137.

Figure 5:
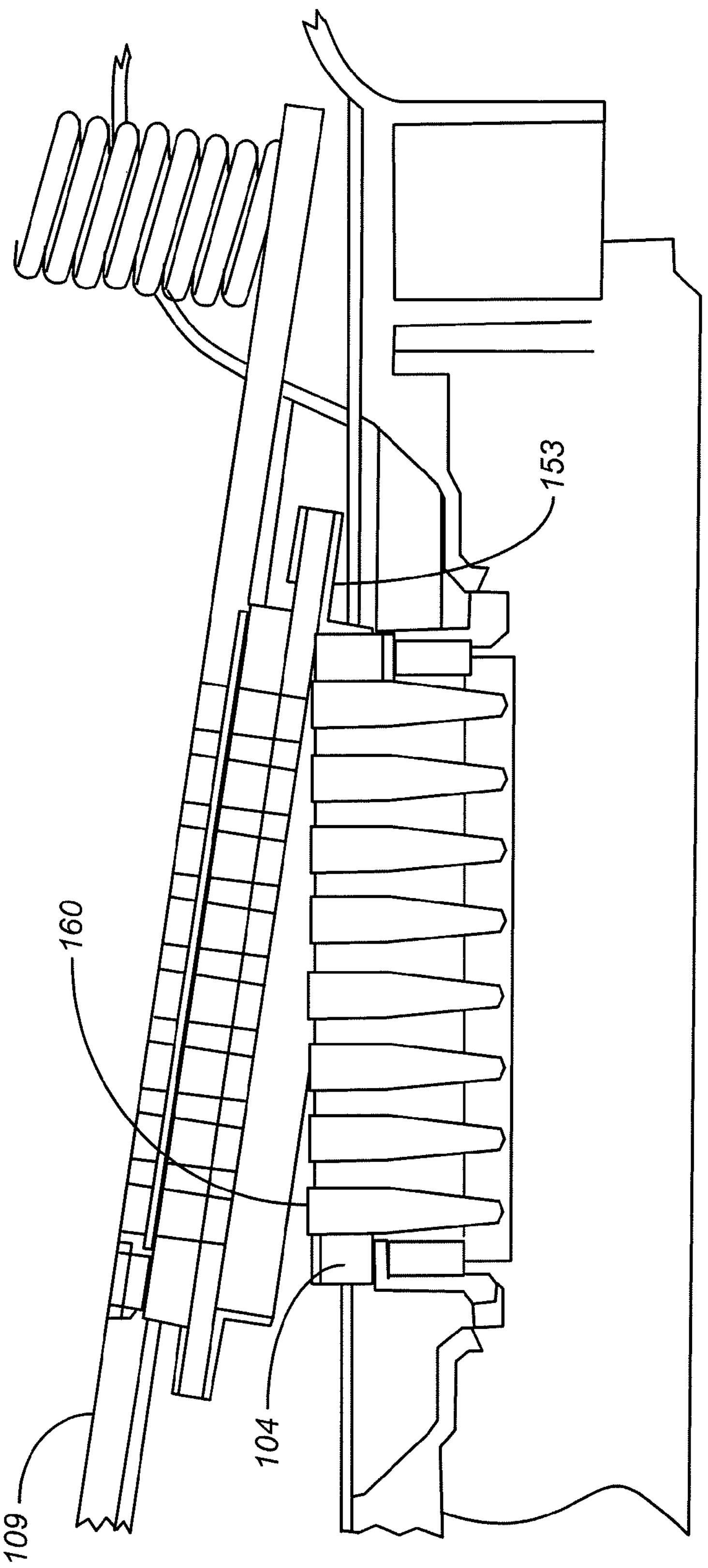
FIG. 5 is a cross section of the base and the pressure plate with a multi-well plate in position in the base.

FIG. 5 is a cross section of the base 102 of the unit, showing a set of reaction vessels 160 (or a multi-well plate) in position over the thermal block 104 with the vessels extending into the depressions of the thermal block. The pressure plate 109 is shown in a slightly raised position above the reaction vessels. When all adjustments have been made and the lid is fully closed, the pressure plate will contact all of the vessels with even pressure. Attached to the pressure plate along the edge nearest the hinge is a sensor 153 that detects the presence of a multi-well plate on the thermal block to differentiate between individual tubes and a multi-well plate. The sensor can be an optical sensor with an associated flag that will flex upon contact with the flange of a typical multi-well plate. The distinction between tubes and a plate can be used to govern the height of the pressure plate and hence the degree of deflection of the springs when the pressure plate is lowered over the tubes or plate. The instrument thus self-adjusts to achieve the spring deflection that will produce the desired force.

Figure 6:
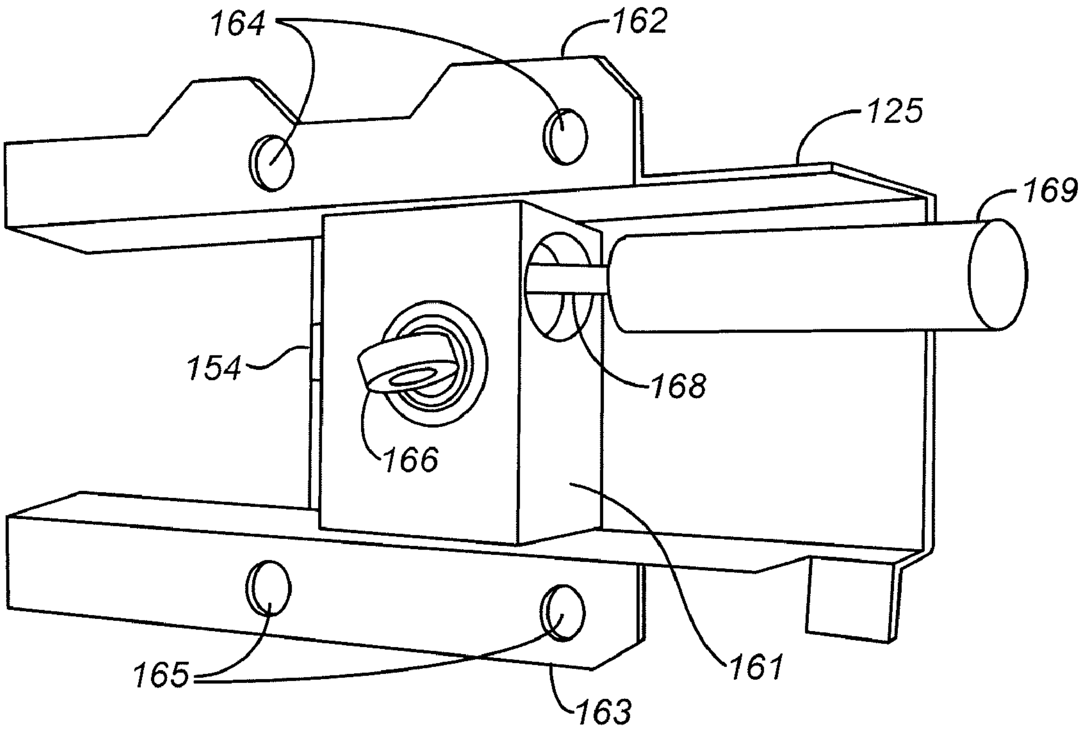
FIG. 6 is a perspective view of one of the components of the lid that control the height of the pressure plate and the self-leveling feature.

The underside of the upper channel 125 is shown in FIG. 6. Mounted in the channel, to the underside of the channel ceiling, is a gear box 161 for a geared connecting rod that controls the height of the pressure plate within the lid and that includes the universal joint providing the self-leveling feature. The channel is mounted to the main frame through mounting fixtures in the ceiling of the channel (not shown). The shoulders 162, 163 along the two lateral sides of the channel have apertures 164, 165 for the guide posts 146, 147, 148, 149 shown in FIG. 3. Protruding downward from the gear box 161 is a rod end 166, i.e., the end of a geared rod (discussed below), and an aperture 167 is shown in one side of the gear box to receive a gear drive 168 extending from a motor 169 that governs the position of (i.e., extends or retracts) the geared rod and hence the rod end 166. A further feature of the upper channel 125 is a home sensor 154 that detects when the rod is in its home position.

Figure 7:
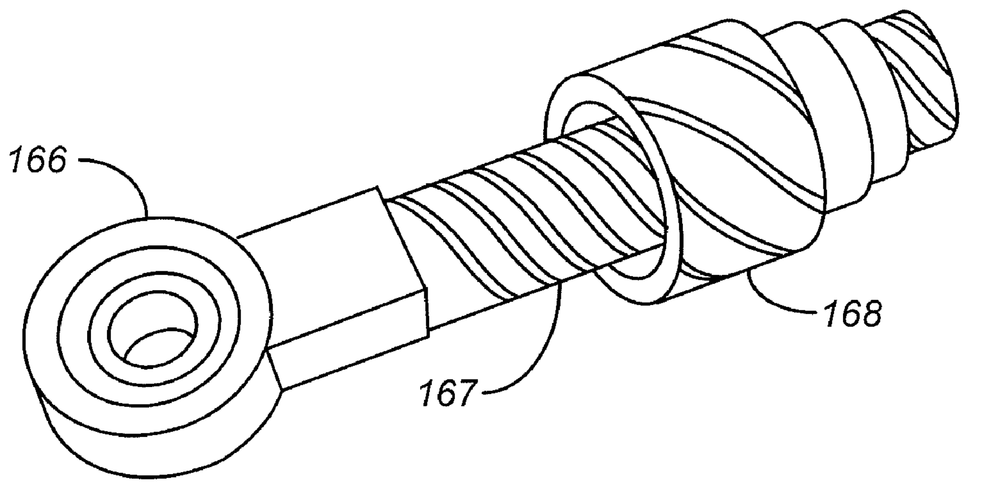
FIG. 7 is a perspective view of one of the components of FIG. 6.

FIG. 7 is an enlarged view of the geared rod 167. A threaded sleeve 168 surrounds the rod, and external gears on the threaded sleeve are engaged by the motor 169 (FIG. 6) to extend or retract the rod 167 and hence the rod end 166. The rod end 166, one example of which is a spherical bearing with a hole passing through it, engages a further, transverse shaft that passes through the center of the rod end and is mounted to the lower channel, as explained further below. Movement of the rod 167 by the motor 169 thereby controls the distance between the upper and lower channels and ultimately the heater plate position. Pivotal freedom of movement of the rod 167 is achieved by bearings in the aperture through which the rod enters the gear box 161. The pivotal movement changes the angle of the rod 167, and hence the angle between the upper and lower channels, which in turn varies the angle of the pressure plate. Bearings in the rod end 166 can themselves provide pivotal freedom of movement. In either case, the rod end 166 and its bearings function as a universal joint.

Figure 8:
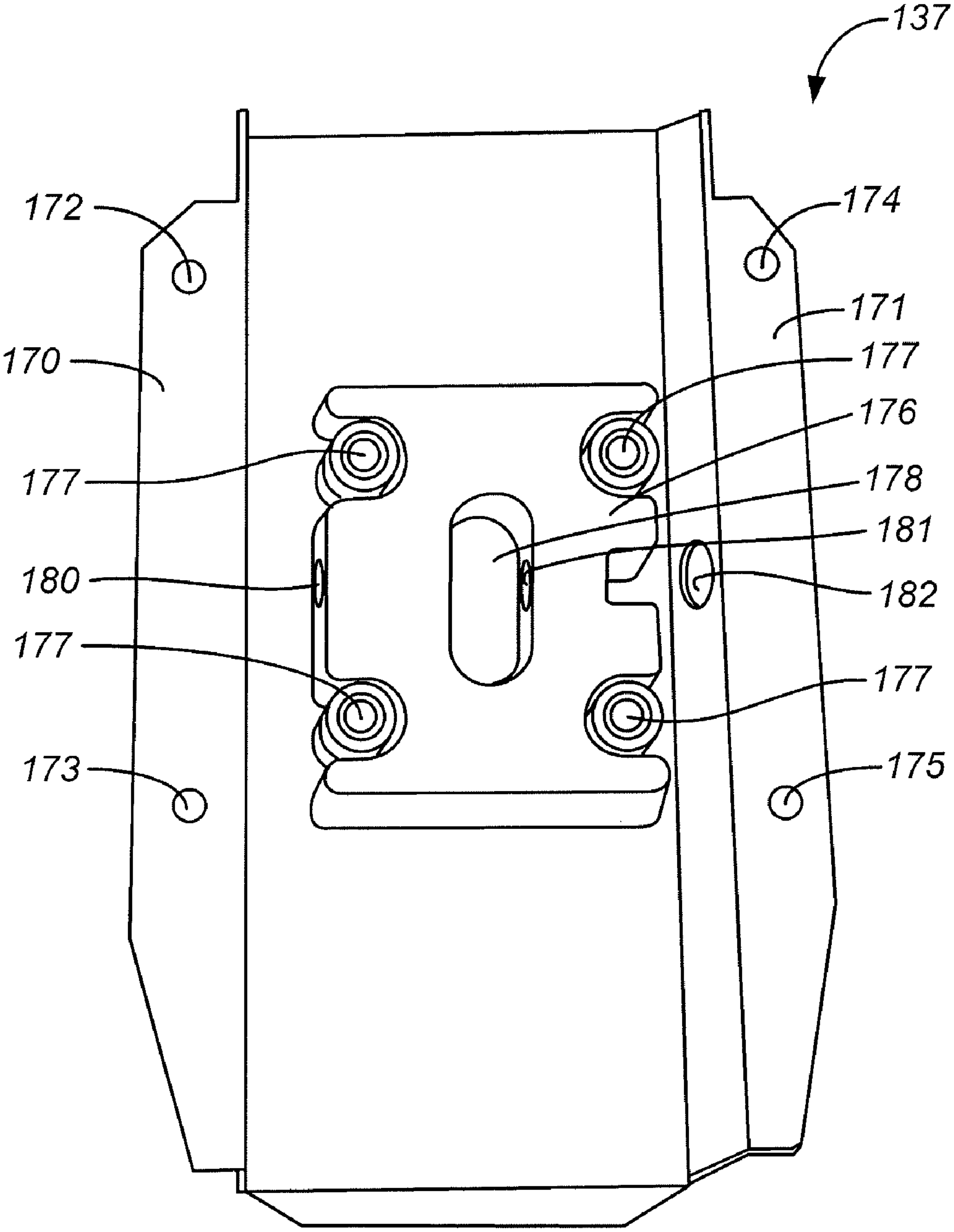
FIG. 8 is a perspective view of another component of the lid that controls the height of the pressure plate.

The lower channel 137 is shown in a top view in FIG. 8. Shoulders 170, 171 along the two lateral sides of the channel have apertures 172, 173, 174, 175 to which the guide posts shown in FIG. 3 are mounted. A pivot block 176 is mounted to the floor of the channel through vibration isolators 177. A slot 178 in the center of the pivot block receives the rod end 166 at the end of the geared rod 167 attached to the upper channel (FIGS. 6 and 7). The transverse shaft (not shown) passing through the rod end will also pass through apertures 180, 181 in the sides of the pivot block as well as apertures 182 (only one of which is visible) in the side walls of the channel. The transverse shaft in this embodiment is the means by which the lid heater carrier assembly hangs from the frame.

Figure 9:
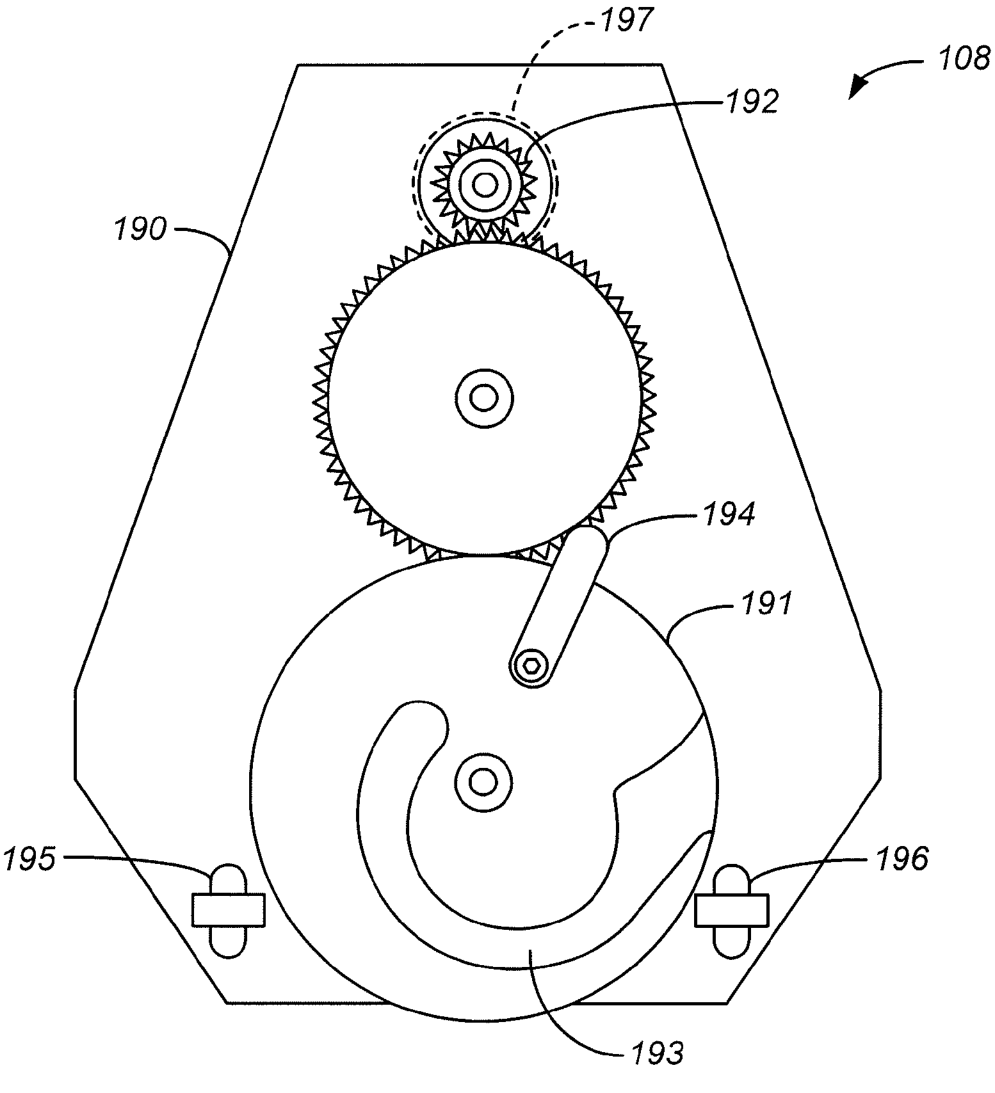
FIG. 9 is a front elevation of the cam-operated mechanism that supplies the final clamping force of the instrument.

FIG. 9 is a front view of the front clamp 108 that is mounted to the front of the lid and that provides the final closure of the pressure plate over the reaction vessels to press the vessels against the thermal block. The clamp includes a bracket plate 190 to which is mounted a gear train with a sufficient gear ratio to provide the torque needed to close the clamp. The gear train terminates in a cam disk 191. (The largest gear is affixed to the rear of the cam disk and not visible in the view shown in FIG. 9.) The pinion gear 192 is driven by a DC gear motor 197 (shown in dashed lines) through an appropriate gear hub mounted to the gear motor which is located behind the bracket plate 190. The cam disk 191 contains a cam groove 193 that, as noted above, engages a protruding pin on the back of the switch pod 106 (FIG. 1), such that counter-clockwise rotation of the cam disk 191 draws the lid down against the base, and the pressure plate against the tubes or the receptacles in the multi-well plate. Mounted to the cam disk 191 is a flag 194 that rotates with the cam disk and operates a pair of optical sensors 195, 196 that disengage the motor when their light beams are intercepted by the flag. The sensors thus define two extremes of the range of travel of the clamp. Alternatives to optical sensors that will likewise function effectively in the apparatus will be apparent to those of skill in the art.

Figure 10:
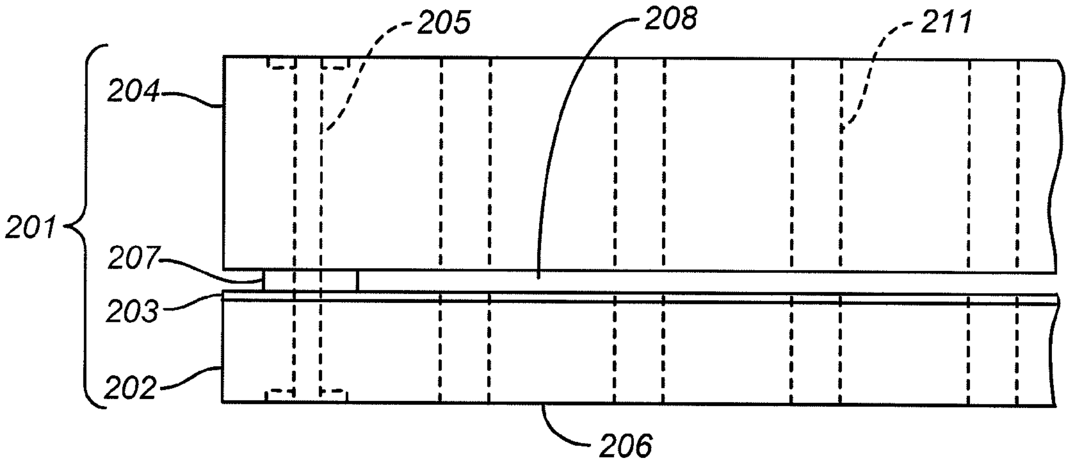
FIG. 10 is an end view of a layered and heated pressure plate for use in the practice of the present invention.
Figure 11:
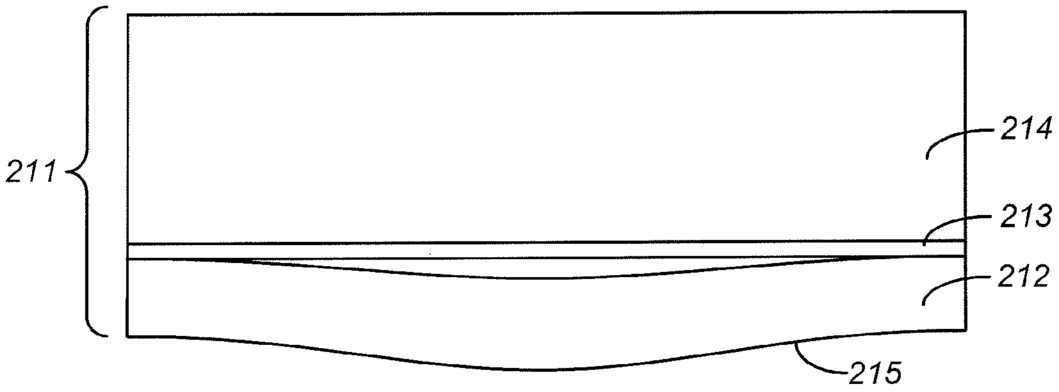
FIG. 11 is an end view of an alternative pressure plate for use in the practice of the present invention.

A specialized example of the pressure plate with a resistance heating element is shown in an end view in FIGS. 10 and 11. As shown in FIG. 10, the pressure plate 201 is a layered plate containing three layers—a lower layer 202, a resistance heating layer 203, and an upper support layer 204, all joined by bolts 205 to form a sandwich-type assembly. In the embodiment shown, one such bolt is positioned close to each of the four corners of the pressure plate. The lower layer 202 has an exposed surface 206 that contacts the sample vessels and presses them against the thermal block. To properly transmit the heat from the resistance heating layer 203 to its undersurface 206 and to spread the heat to promote a uniform temperature at the undersurface, the lower layer 202 is of heat-conductive material, such as aluminum metal. The support layer 204 is preferably of material that is relatively thermally insulating such as a resin, for example, to direct all or most of the heat generated in the heating layer 203 downward through the lower layer 202. In preferred embodiments, a series of spacers 207 are placed between the resistance heating layer 203 and the support layer 204 to leave a gap 208 between the layers. The spacers 207 in this embodiment encircle the bolts 205 that hold the layers together. The purpose of the spacers 207 and the gap 208 is to reduce or eliminate the inherent bowing of the lower, heat-conductive layer 202 when the three layers are compressed against each other by the bolts. By allowing the pressure plate to flex within the limits of the gap, the spacers eliminate the inherent bowing effect from the bolted sandwich assembly and allow the heat conductive layer to adjust in curvature when necessary to promote uniform contact between the pressure plate and the underlying vessels and a uniform force distribution along the length and width of the pressure plate.

FIG. 11 is a further variation of the pressure plate. The pressure plate 211 of FIG. 11 likewise contains three layers—a lower, heat-conductive layer 212, a resistance heating layer 213, and an upper support layer 214, joined together at their peripheries. Here again, the lower layer 212 has an exposed undersurface 215 that serves as the contact surface to press the sample vessels against the thermal block. The lower layer 212 in this variation is constructed of a slightly flexible yet resilient material such as a resilient metal and is bowed away from the other layers to provide the undersurface 214 with a slightly convex contour (the dimensions in the Figure are exaggerated for purposes of demonstration). When pressed against the sample wells and the thermal block, the layers will flatten to provide an even force distribution. In embodiments in which the upper layer 214 and the resistance heating layer 213 can flex to compensate for the bowing effect of the bolts, the gap is not needed.

Figure 12:
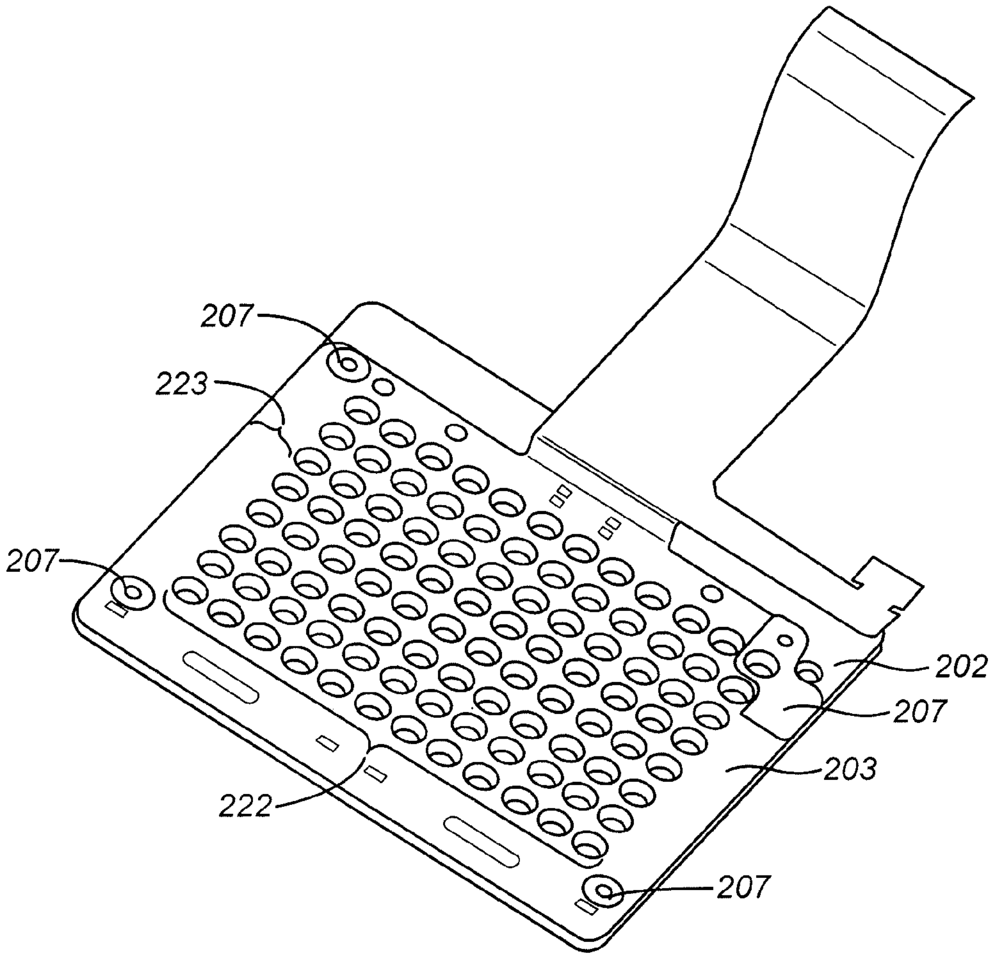
FIG. 12 is perspective view of two of the three layers of the pressure plate of FIG. 10.

FIG. 12 is a perspective view of the lower, heat-conductive layer and the resistance heating layer of the pressure plate of either FIG. 10 or FIG. 11. For convenience, the layers are numbered to correspond to those of FIG. 10. The lower, heat-conductive layer 202 and the resistance heating layer 203 are thus shown, and each one, as well as the support layer 204 (FIG. 10) is apertured, i.e., perforated with an array of holes 221 that have the same size and spacing as the indentations of the thermal block. Thus, when the pressure plate is aligned with the thermal block, the holes allow radiation transmissions and optical signals to and from the sample vessels to emerge from or pass into the space above the pressure plate. The samples can thus be scanned through the pressure plate. The holes occupy a central region 222 of the plate, surrounded by a peripheral region 223, and the spacers 207 are largely located in the peripheral region.

While dimensions in the embodiments of FIGS. 10, 11, and 12 may vary and are not critical to the invention, presently contemplated dimensions are as follows: lower layer thickness, 3 mm; resistance heating layer, 0.3 mm; support layer, 6.4 mm.

Figure 13:
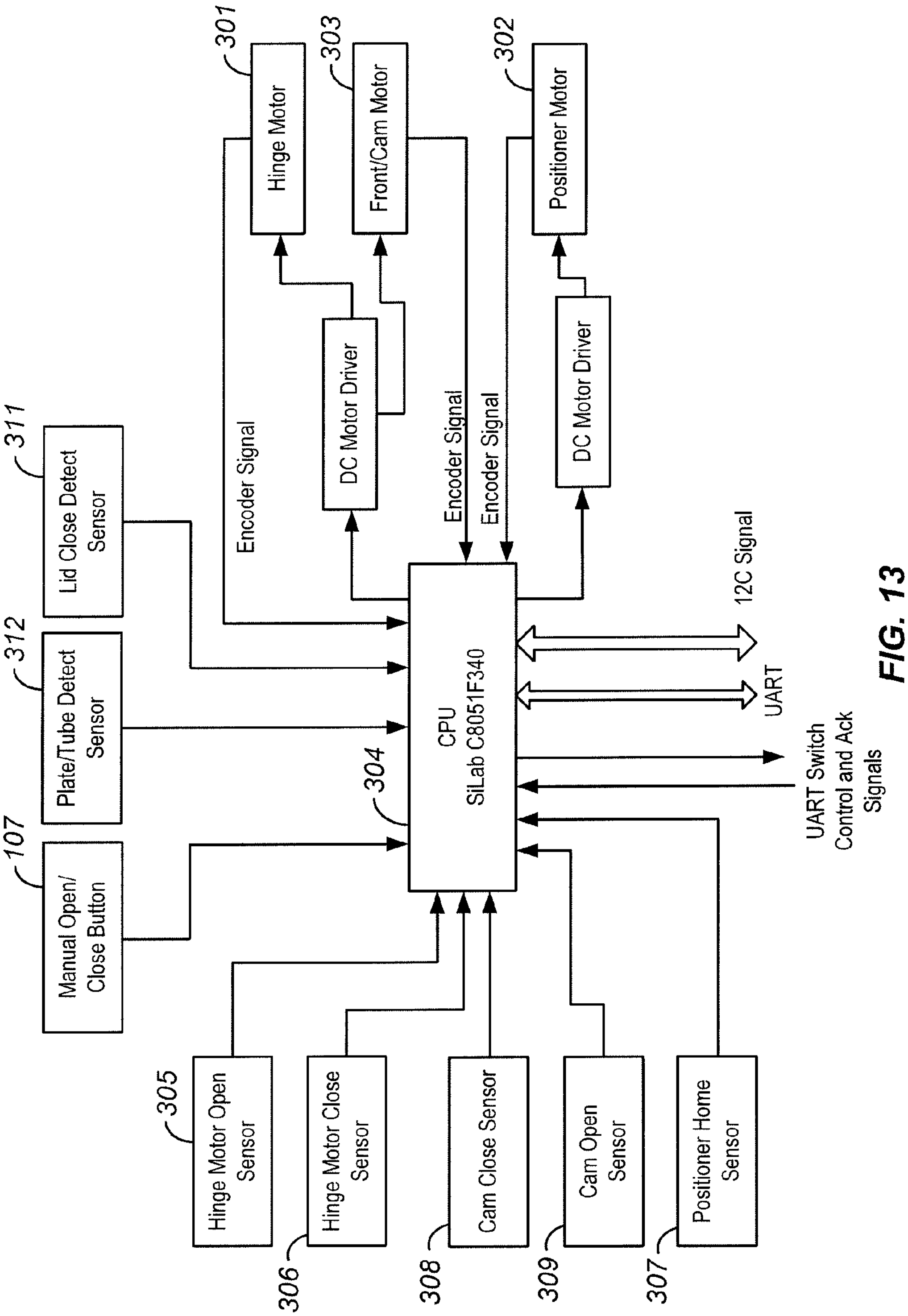
FIG. 13 is a block diagram of the instrument hardware.

FIG. 13 is a block diagram for an example of instrument hardware for an apparatus in accordance with the present invention. The Figure represents an instrument containing three motors, a series of sensors, and a microprocessor. The three motors are the hinge motor 301 the operates the torsion spring hinge assembly 105 (FIG. 1); the position motor 302 that controls the position of the universal joint and shaft that are mounted to the underside of the upper channel 125 (FIG. 2) and control the height of the lower channel 137 (FIG. 3) and hence the pressure plate 109 (FIG. 3); and the cam motor 303 that drives the rotation of the cam disk 191 (FIG. 9). Each motor includes an encoder that detects how far the motor has turned, the encoder thereby controlling the motor by the position of the component that the motor controls. Each encoder sends its signal to the microprocessor 304. The sensors include an open sensor 305 and a closed sensor 306 on the hinge motor to send signals to the microprocessor indicating when either of the two extreme positions of the hinge have been reached, a home sensor 307 on the position universal joint shaft to send a signal indicating when the shaft is at its starting position, and the flag and two optical sensors 308, 309 associated with the cam disk to indicate when the fully open and fully closed positions are reached. Additional sensors include an optical sensor 311 on the front of the lid to indicate whether the lid is open or closed, and one or more plate-vs.-tube sensors 312 to indicate whether the reaction vessels that have been inserted in the unit are in the form of a multi-well plate or a series of tubes that do not occupy all of the positions in the thermal block. Optionally, a still further sensor is included to detect the color of the multi-well plate to allow the optical components to compensate for the color or for reflection from the plate. This additional sensor may also detect mechanical features or bar codes or other indicia on the plate.

The microprocessor 304 is programmed with an embedded algorithm that includes the following steps:

(1) Positioning the pressure plate for an expected (or default) reaction vessel (reaction media) height;

(2) Positioning the lid to exert the pressure plate against the reaction media;

(3) Using the interaction of the pressure plate with the reaction media to determine whether the reaction media height is different than expected;

(4) If the reaction media height is different than expected (i.e., different than the initial setting), repositioning the pressure plate to a different height and repeating steps (2) and (3) a selected number of times; if the comparison continues to fail, noting the presence of an obstruction as an operational error and opening the lid; and (5) Allowing the user to set the force range of the pressure plate.

Referring again to FIG. 13, the position motor 302 is initially set for a relatively shallow (i.e., low-height) multi-well plate and a high force to press the multi-well plate against the thermal block. Initiation of the downward movement of the lid is achieved by manually pressing the button 107 (FIG. 1) in the switch pod or by manually drawing the lid downward until the hinge motor 301 senses the movement and becomes engaged. The microprocessor 304 allows the hinge motor to run until the lid close detect ("ready-to-clamp") sensor 311 at the front of the lid is actuated or the motor stalls. The ready-to-clamp sensor is actuated when the lid is in a position that the cam motor 303 can engage and draw down the lid. When the ready-to-clamp sensor 311 is actuated, the hinge motor

301 is turned off by the microprocessor 304 and the microprocessor verifies through the plate-vs.-tube sensor 312 that a plate has indeed been placed in the instrument rather than individual reaction tubes. If the sensor 312 indicates otherwise (e.g., tubes rather than a plate), the position motor 302 is engaged to re-position the pressure plate to a low-tube and low-force position suitable for individual reaction tubes. If the hinge motor 301 has not stalled by the time the ready-to-clamp sensor 311 is actuated, and the plate-vs.-tube sensor 312 indicates a plate, the default settings of a low-height multi-well plate and maximum force are maintained. If the hinge motor 301 has not stalled by the time the ready-to-clamp sensor 311 is actuated, and the plate-vs.-tube sensor 312 indicates a tube rather than a plate, the position motor 202 is operated to position the pressure plate to a low-tube position and a low-force setting. If the hinge motor 301 stalls before reaching the ready-to-clamp sensor 311, the microprocessor compares the encoder counts from the hinge motor with the range corresponding to a valid tube or plate height. Counts that are outside the range indicate that an obstruction is present, and the procedure is aborted. When this happens, the lid fully opens, and the microprocessor waits for a user response.

If a stall occurs and no obstruction is determined to be present, the microprocessor assumes that a higher plate has been inserted. With information from the plate-vs.-tube sensor 312, the microprocessor selects a new height for the pressure plate. The position motor 302 is then actuated to move to the new height, and the hinge motor 301 is actuated to move the lid to the ready-to-clamp position. The cam motor 303 is then engaged to draw down the lid. Once the lid is lowered to its final position, the reaction sequence can begin, including the movement of the scanner in conjunction with excitations and emission detections.

To summarize, principal functions achieved by the thermal cycler instrument described above are as follows:

- The instrument positions the scanning mechanism in the correct location to allow an optical system to focus on the contents of the reaction vessels both to direct excitation light to the vessel contents and to receive emissions resulting from the excitation.
- The lid opens and closes automatically and automatically positions the pressure plate for reaction vessels or multi-well plates of different heights. If the instrument incorporates a scanning device, the pressure plate contains a matrix of holes aligned with the matrix of depressions in the thermal block which are in turn aligned with the wells of a multi-well plate. The holes allow light to pass between the wells and a scanner mounted within the lid. The pressure plate also contains a resistance heating sheet mounted to the plate by a pressure sensitive adhesive. For instruments that do not contain a scanning device, the holes in the pressure plate can be eliminated.
- The instrument applies the appropriate force to the pressure plate, pressing the reaction vessels against a thermal block while sealing the vessels during the thermal cycling process to eliminate loss of sample through condensation.
- Sensors in the instrument detect whether a multi-well plate or individual tubes have been inserted. Individual tubes generally require less force, since an individual tube is generally supplied with an integrated cap, and also because with individual tubes, the tubes are generally fewer in number than the wells of a multi-well plate and thereby require less force. Control over the force applied by the pressure plate also minimizes the risk of tube deformations caused by the plate.
- The instrument allows the operator to manually override the instrument functions by selecting a particular force or setting the instrument for a particular type of plate or tube.
- The instrument provides a sequence of actions that result in accurate and flexible operation, including sequential actuation of three motors in conjunction with sensors for position adjustments between the motor actuations.
- The lid is torsion-spring-assisted, and thus the hinge motor need only overcome the inertia of the lid. This reduces the motor torque requirement for opening and closing, facilitates the detection of obstructions and of plate or tube heights, and adds to the safety of the instrument by limiting the force exerted by the lid motor.
- The use of a hinge motor for initial placement of the lid and a separate cam motor for the final force application allows for a relatively small hinge motor.
- The universal joint for self-leveling of the pressure plate against the reaction vessels provides an even force distribution, improved sealing, and parallel scanning.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. Apparatus for maintaining a plurality of sample vessels at a uniform temperature by pressing said plurality of sample vessels against a common temperature-controlled heat-conductive block containing indentations complementary in shape to said sample vessels, with a uniform force distribution across all of said sample vessels, said apparatus comprising:

a base configured to receive said block in a fixed position;

a lid joined to said base through a connector permitting raising and lowering of said lid over said base, said lid having mounted thereto a pressure plate having a planar undersurface, said pressure plate positioned on said lid to oppose and align with said block when said lid is lowered, and said pressure plate joined to said lid through a universal joint allowing said pressure plate to pivot upon contact with said plurality of sample vessels to cause said undersurface to contact each of said vessels with substantially equal contact force;

guide means for maintaining vertical alignment of said pressure plate with said block during pivoting of said pressure plate; and clamping means for clamping said lid over said base while causing said pressure plate to press said sample vessels into said indentations at a preselected force.

2. The apparatus of claim 1 wherein said connector joining said lid to said base is a hinge with movement driven by a hinge motor, said clamping means is driven by a clamp motor, and said apparatus further comprises a ready-to-clamp sensor that detects when said lid is closed sufficiently to allow clamping to said base; and a microprocessor governing the actuation of said hinge motor and said clamp motor in response to signals received from said ready-to-clamp sensor.

3. The apparatus of claim 2 wherein said universal joint is joined to said lid by an extendable shaft which varies the height of said pressure plate relative to said lid, and said apparatus further comprises a shaft motor arranged to drive movement of said shaft, actuation of said shaft motor being governed by said microprocessor.

4. The apparatus of claim 3 further comprising a plate-vs.-tubes sensor that differentiates between sample vessels that are joined to form a common plate with an edge flange and sample vessels that are individual tubes not joined to one another, and said microprocessor governs actuation of said shaft motor in response to signals received from said plate-vs.-tubes sensor.

5. The apparatus of claim 4 wherein the microprocessor is programmed to engage said shaft motor to retract said shaft when said ready-to-clamp sensor detects that said lid is lowered to allow clamping to said base and said plate-vs.-tubes sensor does not detect said edge flange.

6. The apparatus of claim 2 wherein said microprocessor is programmed to deactivate said hinge motor when either said ready-to-clamp sensor detects that said lid is lowered sufficiently to allow clamping to said base or that said motor has stalled as a result of an obstruction to the closing of said lid.

7. The apparatus of claim 2 further comprising lid open and lid close sensors to govern the actuation of said hinge motor through said microprocessor.

8. The apparatus of claim 2 wherein said clamping means comprises a cam disk and said clamp motor is a geared motor, and said clamping means further comprises cam position sensors to detect the position of said cam disk and govern the movement of said geared motor.

9. The apparatus of claim 1 wherein said pressure plate is perforated with apertures aligned with said indentations of said block when said block is received within said base to provide optical access to said sample vessels through said pressure plate.

10. The apparatus of claim 1 further comprising a scan head equipped for optical scanning of said sample vessels, said scan head mounted to said lid for traveling along orthogonal axes within a plane parallel to an upper surface of said block.

11. The apparatus of claim 1 further comprising a heat source directing heat to said pressure plate.

12. The apparatus of claim 11 wherein said pressure plate is a layered plate comprising a heat conductive layer forming said planar undersurface, a heat insulating layer, and a resistance heating layer between said heat conductive layer and said heat insulating layer.

13. The apparatus of claim 12 wherein said layered plate is perforated with apertures to provide optical access to sample vessels residing in said indentations of said block, said apertures residing within a central region of said layered plate encircled by a peripheral region, and said layers of said layered plate are joined through fasteners in said peripheral region.

14. The apparatus of claim 13 wherein said layered plate is rectangular in shape with four corners and said fasteners comprise bolts at each of said four corners.

15. The apparatus of claim 13 further comprising spacers encircling said fasteners, said spacers positioned between said resistance heating layer and said heat insulating layer to leave a gap between said resistance heating layer and said heat insulating layer at said central region and thereby allow said heat conductive layer to adjust in curvature when necessary to achieve uniform contact with said sample vessels when said sample vessels.

* * * * *